United States Patent [19]
Yamashita et al.

[11] Patent Number: 6,133,427
[45] Date of Patent: Oct. 17, 2000

[54] ANTI-HUMAN CALCITONIN MONOCLONAL ANTIBODIES AND AN IMMUNOASSAY UTILIZING SAID ANTIBODIES

[75] Inventors: Nobuhiko Yamashita; Manabu Nakamoto, both of Osaka; Kazunobu Miura, Kyoto; Chiwa Kataoka, Kyoto; Junko Sakaki, Kyoto, all of Japan

[73] Assignee: Osaka Gas Company Limited, Osaka, Japan

[21] Appl. No.: 08/997,479

[22] Filed: Dec. 23, 1997

[30] Foreign Application Priority Data

Dec. 24, 1996 [JP] Japan .................................. 8-343165

[51] Int. Cl.[7] .................................................. C12P 21/08
[52] U.S. Cl. .................. 530/388.24; 435/70.21; 530/388.1; 530/388.85
[58] Field of Search ............... 435/70.21; 530/388.1, 530/388.24, 388.85

[56] References Cited

U.S. PATENT DOCUMENTS

| | | | |
|---|---|---|---|
| 4,499,080 | 2/1985 | Duflot et al. ............................. | 530/328 |
| 4,689,220 | 8/1987 | Sturmer et al. ......................... | 424/85.8 |
| 5,330,909 | 7/1994 | Yamashita et al. ................. | 435/240.27 |

OTHER PUBLICATIONS

Seth, R., et al., J. Endocrinol 119, 351–357 (1988).
Motte, P., et al., The Journal of Immunology, 138, 3332–3338 (May 1987).
Hellstrom, K. E., et al., in Monoclonal Antibodies for Cancer Detection and Therapy (Baldwin et al., eds.), p. 20, 1985, Academic Press, London.
Scopsi, L., Histochemistry, 88, 113–125 (1988).
Motte, P., et al., Henry Ford Hosp. Med. J., 35, Nos. 2 & 3, 129–132 (1987).
Racchetti, G., et al., Molecular Immunology, 24, 1169–1179 (1987).

*Primary Examiner*—Laurie Scheiner

[57] ABSTRACT

Monoclonal antibodies having a high affinity for human calcitonin, particularly monoclonal antibodies suitable for a sandwich immunoassay are disclosed. Also disclosed are hybridomas producing said monoclonal antibodies and a sandwich immunoassay utilizing said antibodies for determining human calcitonin in blood.

2 Claims, 1 Drawing Sheet

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 32 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

```
Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30
```

(2) INFORMATION FOR SEQ ID NO:2:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

```
Cys Gly Asn Leu Ser Thr Cys Met Leu Gly
1               5                   10
```

(2) INFORMATION FOR SEQ ID NO:3:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

```
Thr Tyr Thr Gln Asp Phe Asn Lys Phe His
1               5                   10
```

(2) INFORMATION FOR SEQ ID NO:4:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

```
Thr Phe Pro Gln Thr Ala Ile Gly Val Gly Ala Pro
1               5                   10
```

(2) INFORMATION FOR SEQ ID NO:5:

(i) SEQUENCE CHARACTERISTICS:
       (A) LENGTH: 20 amino acids

-continued

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Gly Asn Leu Ser Thr Cys Met Leu Gly Thr Tyr Thr Gln Asp Phe
1               5                   10                  15

Asn Lys Phe His
            20

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Thr Tyr Thr Gln Asp Phe Asn Lys Phe His Thr Phe Pro Gln Thr Ala
1               5                   10                  15

Ile Gly Val Gly Ala Pro
            20
```

ANTI-HUMAN CALCITONIN MONOCLONAL ANTIBODIES AND AN IMMUNOASSAY UTILIZING SAID ANTIBODIES

FIELD OF THE INVENTION

The present invention relates to monoclonal antibodies having a high affinity for human calcitonin, particularly monoclonal antibodies suitable for a sandwich immunoassay. The monoclonal antibodies can be used to quantify the human calcitonin produced in blood in a high sensitivity, and to precisely judge the kinetic of the human calcitonin in blood for treatment or diagnosis.

PRIOR ART

Calcitonin (CT) is a peptide hormone constituted of 32 amino acids and secreted from thyroid gland C-cells in mammals. Although an action to decrease calcium levels in blood by inhibiting bone absorption in bone and an action to decrease phosphorus levels in serum by accelerating excretion of inorganic phosphorus into urine in the kidney as well as other actions are known as physiological actions of this hormone, many actions are still unknown.

Currently, determination of human calcitonin (hCT) in blood is carried out by a radioimmunoassay (RIA) and utilized for diagnosis of thyroid medullary carcinoma, observation of its therapeutical process, screening of familial thyroid medullary carcinoma, and diagnosis of ectopic hCT-producing tumors. However, a commercially available RIA kit utilizes an anti-hCT polyclonal antibody which is a mixture of antibodies against various epitopes. Accordingly, the kit may also determine decomposition products in blood other than the monomer hCT. Thus, it is believed that hCT in blood can not be accurately determined by the RIA method utilizing such a polyclonal antibody. In addition, its sensitivity is relatively low, in the order of 30 pg/ml, and therefore, it is not possible to accurately determine a concentration of hCT in the blood of normal people.

On the other hand, a monoclonal antibody (MAb) specifically bound to hCT recognizes only a particular portion (epitope) of hCT and binds to it. Accordingly, it is possible to construct a determination system which is specific and sensitive. In particular, it is believed that construction of a sandwich immunoassay, which utilizes two monoclonal antibodies recognizing different epitopes of hCT, enables the specific determination of monomer hCT only without the interference due to decomposition products, etc.

The sandwich immunoassay is a measuring technique utilizing two monoclonal antibodies recognizing different epitopes. One monoclonal antibody (primary antibody) is immobilized to a solid phase and then reacted with a sample, by which an antigen in the sample is immobilized to the solid phase through the primary antibody. Then, the other monoclonal antibody (secondary antibody), which is labelled, is reacted with the immobilized antigen, by which the labelled secondary antibody is immobilized to the solid phase through the immobilized antigen. Finally, the immobilized labelling substance can be detected to determine the amount of the antigen in the sample.

In order to construct a sandwich immunoassay having a high sensitivity, it is necessary to search a suitable combination of monoclonal antibodies for the sandwich immunoassay. For the search of such an optimal combination of monoclonal antibodies, it is necessary to construct sandwich immunoassays using all the combinations of available monoclonal antibodies and to select a combination of monoclonal antibodies which exhibits the highest sensitivity.

Presently, there are several reports on sandwich immunoassays which determine hCT in blood and it is confirmed that the sandwich immunoassays are superior to RIA methods in terms of both sensitivity and accuracy. However, the sensitivity of these sandwich immunoassays is still unsatisfactory for the determination of human calcitonin levels in the blood of normal people.

In view of the known fact that the amount of human calcitonin in the blood increases specifically responding to thyroid medullary carcinoma and malignant tumors in other organs, the present inventors have already prepared monoclonal antibodies which specifically react to human calcitonin for the purpose of precisely and simply judging the kinetic of the human calcitonin in blood in thyroid medullary carcinoma and malignant tumors in other organs, and have a patent application for the subject matter [Japanese Patent Publication (Kokai) No. 103689/1993; U.S. Pat. No. 5,330,909]. However, we found that, if these monoclonal antibodies are used for a sandwich immunoassay, there is no combination of the monoclonal antibodies which gives a satisfactory sensitivity.

BRIEF DESCRIPTION OF THE INVENTION

The present invention provides a monoclonal antibody having a high sensitivity which enables the determination of human calcitonin concentrations in the blood of normal people with high sensitivity in a sandwich immunoassay. The present invention also provides a hybridoma producing said antibody and a sandwich immunoassay utilizing said antibody for sensitively and rapidly determining human calcitonin.

Now, the present inventors newly selected monoclonal antibodies which enable the detection of human calcitonin with high sensitivity using the sandwich immunoassay, by establishing hybridoma cell lines producing anti-human calcitonin monoclonal antibodies by a cell fusion method and then examining the optimal combination of the resulting monoclonal antibodies for the immunoassay. As a result, it was found that particular combinations of monoclonal antibodies as shown in the Examples below give a high sensitivity, particularly in the sandwich immunoassay.

It was found that a monoclonal antibody produced by a hybridoma cell line selected from the group consisting of hybridomas HCT-M-02, HCT-C-08, HCT-N-11, HCT-C-15, HCT-M-16 and HCT-C-18 is particularly suitable for the above purpose.

DETAILED DESCRIPTION OF THE INVENTION

Figure 1:
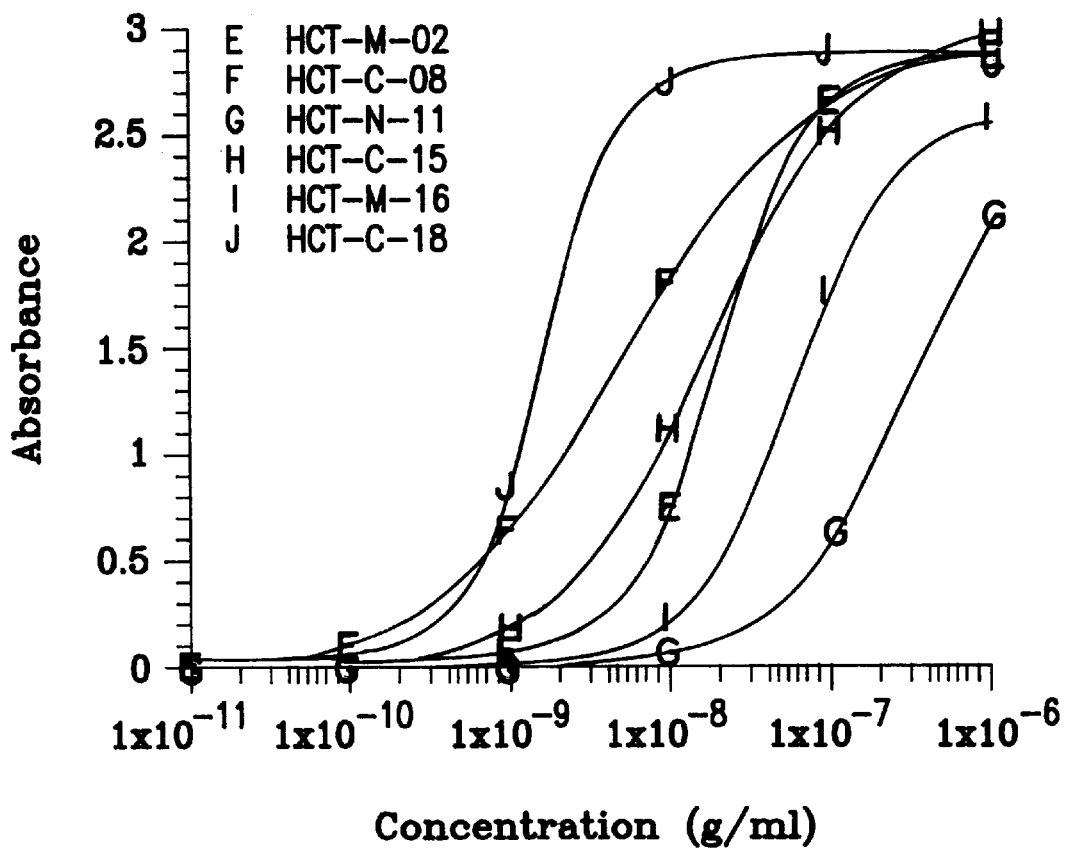
FIG. 1 is a graph showing the results of determining a correlation of concentrations of antibodies and reactivities with an antigen for the present monoclonal antibodies.

The present monoclonal antibodies can be prepared by a cell fusion method. Thus, the desired monoclonal antibodies can be obtained by (i) fusing antibody-producing cells with myeloma cells to form hybridomas, (ii) cloning the hybridomas and selecting clones showing a specificity to human calcitonin, and (iii) cultivating the clones and recovering the monoclonal antibodies produced.

The antibody-producing cells may be, for example, spleen cells or lymph node-derived B cells from an animal immunized with an immunogen mixture which is prepared by mixing human calcitonin or a human calcitonin conjugate optionally bound to a carrier protein with a suitable adjuvant.

Animals such as mice, rats, rabbits and goats may be used as the animals to be immunized.

Human calcitonin used as an antigen can be chemically synthesized. For the preparation of a human calcitonin conjugate, ovalbumin can be exemplified as a carrier protein and 1-ethyl-3-(3-dimethylaminopropyl)-carbodiimide can be exemplified as a cross-linking reagent.

Immunization may be carried out, for example, by administering 4 to 40 mg of the human calcitonin conjugate into the peritoneal cavity of an animal, 3 or 4 times at intervals of 2 to 3 weeks. After three days from the final booster immunization, the antibody-producing cells are recovered from the immunized animal.

The cell fusion of the antibody-producing cells with myeloma cells may be carried out by a conventional method. The myeloma cells derived from mice, rats or humans may be used. The cell fusion may be carried out using, for example, a polyethylene glycol method or an electrical fusion method.

The selection of hybridomas obtained by the cell fusion may be carried out, for example, by radioimmunoassay, enzyme-labelled immunoassay (ELISA) or fluorescence-labelled immunoassay. Thus, human calcitonin is allowed to react with a supernatant of a hybridoma culture, and the hybridomas producing an antibody which shows specificity to human calcitonin are selected and then cloned by a limiting dilution method.

The recovery of the monoclonal antibody can be carried out in the following manner, for example. The selected clones are implanted, for example, into the peritoneal cavity of a mouse previously administered with pristan (2,6,10,14-tetramethylpentadecan), and the ascites fluid of the mouse containing the monoclonal antibody is recovered after 10 to 14 days from the implantation. The recovery of the monoclonal antibody from the ascites fluid is easily accomplished by ammonium sulfate precipitation, ion-exchange chromatography, affinity chromatography, or the like.

The search of the optimal combination of monoclonal antibodies for the sandwich immunoassay is usually carried out by examining sandwich immunoassays using all the combinations of the monoclonal antibodies prepared and by finding the combinations of monoclonal antibodies exhibiting the highest sensitivity.

Using the resulting monoclonal antibodies, it is possible to specifically and sensitively determine human calcitonin in the living body, for example, in serum or plasma. For measurement, the antibodies can be labelled with an enzyme, a fluorescent substance, a radioisotope or the like. Furthermore, it is possible to carry out immunological assays such as a sandwich-type enzyme immunoassay (EIA), fluoroimmunoassay (FIA) or radioimmunoassay (RIA) according to the procedures usually used in these assays.

EXAMPLES

The present invention is further illustrated by the following Examples, but should not be construed to be limited thereto.

Example 1
Preparation of anti-human calcitonin monoclonal antibodies
(1) Preparation of antigen A human calcitonin peptide consisting of 32 amino acids as shown in Table 5 below was synthesized by a conventional peptide synthesis. In order to enhance the immunogenicity of the peptide antigen, it was bound to a carrier protein using a cross-linking reagent. Thus, 10 mg/ml of aqueous ovalbumin solution (16.8 µl) and 100 mg/ml of 1-ethyl-3-(3-dimethylaminopropyl)carbodiimide (16.8 µl) were added to 25 mg/ml of aqueous human calcitonin solution (22.4 µl), and the mixture was reacted overnight. The reaction solution was dialyzed against distilled water, and then adjusted to a human calcitonin conjugate solution containing 10 mg/ml of human calcitonin.

(2) Immunization of mouse

The human calcitonin conjugate solution (100 µl) containing 10 mg/ml of human calcitonin was mixed with Freund's complete adjuvant (100 µl). Balb/c mice were immunized by administering the mixture (200 µl) into the peritoneal cavity of the animals, 3 or 4 times at intervals of 2 to 3 weeks.

(3) Cell fusion

After 20 to 40 days from the final immunization, 10 mg/ml of human calcitonin (100 µl) was administered to the animals every day for 3 days, and after 3 days from the final administration, the spleen was removed from the mice and spleen cells were recovered. Mouse myeloma cells (P3X63Ag8U1) were previously cultivated using a DMEM solution containing 15% fetal bovine serum in a $CO_2$ incubator at 37° C. Then, $0.5-1\times10^8$ of the spleen cells and $2\times10^7$ of the myeloma cells were charged into 50 ml of a centrifuge tube and mixed thoroughly. Then, 75 mM HEPES solution (0.5 ml) containing 50% polyethylene glycol 1500 was added to the mixed cells, and the mixture was gently mixed to drive the cell fusion of the spleen and myeloma cells. A DMEM solution (40 ml) was added to the cell mixture with gentle stirring within about 10 minutes, and then, a DMEM solution (30 ml) containing 15% fetal bovine serum was added to the cell mixture with gentle stirring within about 10 minutes. The cell fusion procedure was carried out at 37° C. The solution (70 ml) containing fused cells was added to each well of two 96-well plates and cultivation was carried out overnight in a $CO_2$ incubator at 37° C. Fused cells and unfused myeloma cells were selected in a HAT medium. Thus, one half (0.1 ml) of the overnight cultured medium was replaced with a DMEM solution containing 10 µM hypoxanthine, 0.4 µM aminopterin, 16 µM thymidine and 15% fetal bovine serum (HAT medium), and the cultivation in the $CO_2$ incubator at 37° C. was continued to kill the unfused myeloma cells.

(4) Screening and cloning of antibody-producing hybridomas

Screening of the hybridomas was carried out by a radioimmunoassay. Each supernatant (100 µl) was taken from the wells in which the proliferation of hybridomas was observed, and $^{125}$I-labelled human calcitonin (100 µl) and unlabelled human calcitonin (100 µl) were added to and reacted with the supernatant. Then, 50% polyethylene glycol 6000 (100 µl) was added to the reaction mixture to allow the precipitation of the reaction products, and the radioactivity of the precipitate was measured. Hybridomas in the wells, in which the production of an antibody was confirmed, were cloned by a limiting dilution method. The hybridomas were cultivated in a RPMI 1640 medium containing 15% fetal bovine serum. By the above procedures, 18 clones were established.

(5) Large preparation and purification of monoclonal antibody

Pristan (2,6,10,14-tetramethylpentadecan; Wako Junyaku Co.) (0.5 ml) was intraperitoneally injected to mice, and the mice were bred over 2 weeks. Monoclonal antibody-producing hybridomas which were previously proliferated were recovered and diluted with DMEM to about $4\times10^6$/ml of cell concentrations. The cell solutions (0.5 ml each) were intraperitoneally injected into the mice. One to three weeks after the injection, the abdomen of the mice was cut out and ascites fluid was recovered with a Pasteur pipet. After the ascites fluid taken was mixed with an equal amount of a hemolysate, the mixture was centrifuged at 2,000 rpm for 10 minutes. The resultant supernatant was used as a monoclonal antibody solution.

From the monoclonal antibody solutions thus obtained, monoclonal antibodies were purified by Protein A column chromatography using a mouse IgG purification kit [Affigel Protein A MAPS-II, Bio-Rad Laboratories Co. Ltd].

Example 2
Selection of optimal monoclonal antibodies for sandwich immunoassay Optimal monoclonal antibodies for the sandwich immunoassay were selected by carrying out the sandwich immunoassay using the monoclonal antibodies obtained in Example 1.

The purified monoclonal antibodies were biotin-labelled using Biotinilation Kit (Amersham). The purified monoclonal antibodies were desalted with a NAP-25 column and quantified. Then, the monoclonal antibodies (1 mg each) were separately poured into wells and freeze-dried. The freeze-dried samples were dissolved in a 50 mM sodium borate buffer (pH 8.6) (1 ml) and the biotinilation reagent (40 μl) was added to and reacted with the solutions with shaking at room temperature for one hour. The unreacted reagent was removed using the NAP-25 column and 100 mM $NaN_3$ (180 μl) was added to the resulting solutions to obtain biotin-labelled monoclonal antibodies.

The sandwich immunoassay was carried out using all the combinations of 18 primary antibodies with 18 secondary antibodies. Each well of Microtiter plates (Costar) was filled with the primary antibodies [50 mM carbonate buffer (pH 9.6) containing 10 μg/ml purified antibody] (50 μl). After the wells were allowed to stand at 4° C. overnight, the primary antibodies were removed from the wells. The wells were washed with PBS and then filled with a blocking solution [4-fold diluted Block Ace (Yukijirushi Nyugyo Co.)] (200 μl). After the wells were allowed to stand at room temperature for one hour, the blocking solution was removed from the wells. The wells were washed with PBS-Tween and then filled with an antigen solution (10-fold diluted Block Ace solution containing 5 ng/ml hCT) (50 μl). After the wells were allowed to stand at room temperature for two hours, the antigen solution was removed from the wells. The wells were washed with PBS-Tween and then filled with secondary antibodies [10-fold diluted Block Ace solution containing 100-fold diluted biotin-labelled antibodies] (50 μl). After the wells were allowed to stand at room temperature for two hours, the secondary antibodies were removed from the wells. The wells were washed with PBS-Tween and then filled with an enzyme solution [10-fold diluted Block Ace solution containing 500-fold diluted HRP-streptavidin (Amersham)] (50 μl). After the wells were allowed to stand at room temperature for two hours, the enzyme solution was removed from the wells. The wells were washed with PBS-Tween and then filled with a substrate solution [100 mM citrate buffer (pH 4.5) containing 12 mg/ml o-phenylenediamine] (200 μl). The mixture was allowed to react at room temperature for 15 minutes, the reaction was terminated by adding 6N $H_2SO_4$ (50 μl), and absorbance was measured at 490 nm.

The results of the determination of human calcitonin obtained by carrying out the sandwich immunoassay using all the combinations of 18 monoclonal antibodies are shown in Table 1 below.

TABLE 1

Detection of hCT by sandwich immunoassay

| 1st MAb | 2nd MAb | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| 1 | | − | ± | + | − | − | − | − | ± | + | − | − | ± | ± | − | − | − | + |
| 2 | − | | − | ++ | − | − | ++ | +++ | − | ++ | + | − | + | + | − | + | − | − |
| 3 | ++ | − | | − | − | − | − | − | ± | − | ± | − | − | ± | − | ± | + | − |
| 4 | − | − | − | | − | ± | − | − | ++ | − | − | − | − | − | − | − | − | − |
| 5 | − | − | ± | − | | − | − | − | − | − | ± | − | + | + | − | ± | − | ± |
| 6 | − | − | − | − | − | | ++ | − | − | − | − | ± | − | ± | − | + | − | − |
| 7 | + | + | + | − | ++ | + | | − | − | + | − | + | ++ | + | − | + | − | + |
| 8 | − | − | ± | − | − | − | ± | | − | ± | +++ | − | − | − | + | ± | − | − |
| 9 | − | ± | − | + | − | ++ | ± | − | | − | ± | + | − | ++ | − | − | ± | − |
| 10 | ± | − | − | − | − | ± | + | − | ++ | | − | − | − | + | ± | − | + | − |
| 11 | − | + | ± | − | − | + | − | ± | ± | − | | − | − | ++ | − | ++ | − | − |
| 12 | ± | − | − | + | − | − | ++ | − | − | − | − | | − | ++ | − | − | − | + |
| 13 | − | − | − | ± | ± | − | ± | − | + | ± | − | ± | | − | ± | − | − | − |
| 14 | − | − | + | − | + | − | + | + | ++ | + | ++ | − | − | | − | + | − | ++ |
| 15 | + | − | − | − | − | ± | − | − | − | − | − | ± | − | − | | +++ | − | ± |
| 16 | − | − | ± | ± | − | + | − | − | − | − | +++ | − | ++ | − | − | | − | − |
| 17 | − | − | − | − | − | − | − | + | − | − | − | − | − | − | − | − | | − |
| 18 | − | +++ | − | − | − | ++ | + | − | − | + | ++ | − | + | − | + | − | ± | |

+++: above 2.0 of absorbance at 490 nm
++: 1.0 to 2.0 of absorbance at 490 nm
+: 0.5 to 1.0 of absorbance at 490 nm
±: 0.2 to 0.5 of absorbance at 490 nm
−: below 0.2 of absorbance at 490 nm As a result, it was found that human calcitonin can be determined in a high sensitivity by the sandwich immunoassay utilizing the combinations (a) to (e) of monoclonal antibodies as shown in Table 2 below. Table 2: Optimal combination of MAbs in sandwich immunoassay Combination Primary MAb Secondary MAb

TABLE 2

Optimal combination of MAbs in sandwich immmunoassay

| Combination | Primary MAb | Secondary MAb |
|---|---|---|
| (a) | No. 2 (HCT-M-02) | No. 8 (HCT-C-08) |
| (b) | No. 16 (HCT-M-16) | No. 11 (HCT-N-11) |
| (c) | No. 8 (HCT-C-08) | No. 11 (HCT-N-11) |
| (d) | No. 15 (HCT-C-15) | No. 16 (HCT-M-16) |
| (e) | No. 18 (HCT-C-18) | No. 2 (HCT-M-02) |

The six hybridomas HCT-M-02, HCT-C-08, HCT-N-11, HCT-C-15, HCT-M-16 and HCT-C-18 (producing MAbs No. 2, No. 8, No. 11, No. 15, No. 16 and No. 18, respectively) mentioned in Table 2 were deposited to National Institute of Bioscience and Human-Technology, Agency of Industrial Science and Technology (1–3, Higashi 1-chome Tsukuba-shi Ibaraki-ken 305, JAPAN) under the Budapest Treaty on Nov. 21, 1996, and obtained the accession numbers of FERM BP-5750, FERM BP-5752, FERM BP-5749, FERM BP-5753, FERM BP-5751 and FERM BP-5754, respectively.

Example 3

Characterization of monoclonal antibodies

Next, the characteristics of six monoclonal antibodies which constitute the combinations as shown in the above Table 2 were examined.

(1) Analysis of isotype

The six monoclonal antibodies selected were analyzed for their isotypes. Firstly, 0.25 ng/ml of synthesized human calcitonin (50 μl) was added to each well of an ELISA plate (Costar) and allowed to react at 37° C. for one hour to immobilize the antigen to the wells. A blocking agent (300 μl) was then added to the wells and the wells were incubated at 37° C. for two hours. Then, each of the purified antibodies (5 to 50 ng) was added to the wells and allowed to react at 37° C. for one hour. After washing the wells, the antibodies (50 μl) corresponding to various isotypes attached to Mouse Typer Sub-Isotyping Panel (Bio-Rad Laboratories) were added to the wells and allowed to react at 37° C. for one hour. Then, a peroxidase-labelled antibody (50 μl) was added to the wells and the wells were allowed to stand at room temperature for one hour. After thoroughly washing the wells, the reaction was terminated by adding 2M sulfuric acid and absorbance was measured at 490 nm (measuring wavelength) and at 655 nm (control wavelength).

As shown in Table 3, it was found that the monoclonal antibodies produced by clones HCT-C-15 and HCT-M-16 belong to isotype IgG2a and the monoclonal antibodies produced by the other clones belong to isotype IgG1 and that all the L chains of these antibodies are K chains. These results are summarized in Table 4.

TABLE 4

Isotype of MAbs produced by six clones

| Clone name | Isotype |
| --- | --- |
| HCT-M-02 | IgG1 |
| HCT-C-08 | IgG1 |
| HCT-N-11 | IgG1 |
| HCT-C-15 | IgG2a |
| HCT-M-16 | IgG2a |
| HCT-C-18 | IgG1 |

(2) Analysis of epitope site

Synthesized human calcitonin peptides ($3.4 \times 10^{-11}$ mole) were added to wells of an ELISA plate (Costar) and allowed to react at 37° C. for one hour to immobilize the antigens to the wells. After washing the wells, a blocking agent (300 μl) was added to the wells and the wells were incubated at 37° C. for two hours. Then, each of the purified antibodies (5 to 50 ng) was added to the wells and allowed to react at 37° C. for one hour. After a 3000-fold diluted peroxidase-labelled anti-mouse IgG (recognizing γ-chain) antibody (50 μl) was added to the wells and allowed to react at room temperature for one hour, a 0.1% o-phenylenediamine solution (50 μl) containing 0.15% $H_2O_2$ was added to the wells and allowed to react at room temperature for 10 minutes. The reaction was terminated by adding 2M sulfuric acid and absorbance was measured at 490 nm (measuring wavelength) and at 655 nm (control wavelength).

The sequences of the synthesized human calcitonin (hCT) peptides used for the analysis of epitope sites are as shown in Table 5 below.

TABLE 3

Analysis of isotype by ELISA

| Clone | IgG1 | IgG2a | IgG2b | IgG3 | IgM | IgA | κ | λ |
| --- | --- | --- | --- | --- | --- | --- | --- | --- |
| HCT-M-02 | 2.413 | 0.374 | 0.165 | 0.172 | 0.056 | 0.064 | 3.000 | 0.097 |
| HCT-C-08 | 2.512 | 0.121 | 0.082 | 0.042 | 0.088 | 0.102 | 1.625 | 0.050 |
| HCT-N-11 | 1.674 | 0.056 | 0.019 | 0.084 | 0.049 | 0.000 | 0.556 | 0.000 |
| HCT-C-15 | 0.383 | 1.936 | 0.159 | 0.162 | 0.093 | 0.153 | 1.405 | 0.142 |
| HCT-M-16 | 0.030 | 1.971 | 0.103 | 0.040 | 0.018 | 0.024 | 1.099 | 0.019 |
| HCT-C-18 | 2.217 | 0.353 | 0.611 | 0.103 | 0.063 | 0.035 | 1.894 | 0.028 |

TABLE 5

Synthesized hCT peptides used

| | | |
|---|---|---|
| hCT(1–32): | CGNLSTCMLGTYTQDFNKFHTFPQTAIGVGAP-NH$_2$ | SEQ ID NO:1 |
| hCT(1–10): | CGNLSTCMLG | SEQ ID NO:2 |
| hCT(11–20): | TYTQDFNKFH | SEQ ID NO:3 |
| hCT(21–32): | TFPQTAIGVGAP-NH$_2$ | SEQ ID NO:4 |
| hCT(1–20): | CGNLSTCMLGTYTQDFNKFH | SEQ ID NO:5 |
| hCT(11–32): | TYTQDFNKFHTFPQTAIGVGAP-NH$_2$ | SEQ ID NO:6 |

The results of the analysis of epitope sites are shown in Table 6 below. As summarized in Table 7, the anti-hCT monoclonal antibodies produced by the six clones recognized N-terminal, central or C-terminal portions of human calcitonin.

TABLE 6

Analysis of epitope sites by ELISA

| | Peptide | | | | | |
|---|---|---|---|---|---|---|
| Clone | hCT1–32 | hCT1–10 | hCT11–20 | hCT21–32 | hCT1–20 | hCT11–32 |
| HCT-M-02 | 3.000 | 0.030 | 2.628 | 0.818 | 2.882 | 2.763 |
| HCT-C-08 | 3.000 | 0.110 | 0.045 | 3.000 | 0.415 | 3.000 |
| HCT-N-11 | 0.783 | 0.057 | 0.036 | 0.054 | 0.486 | 0.024 |
| HCT-C-15 | 3.000 | 0.025 | 0.143 | 0.840 | 0.117 | 3.000 |
| HCT-M-16 | 2.181 | 0.027 | 0.493 | 0.017 | 1.692 | 2.115 |
| HCT-C-18 | 3.000 | 0.026 | 0.030 | 3.000 | 0.150 | 3.000 |

TABLE 7

Epitope site of MAbs produced by six clones

| Clone name | Epitope site |
|---|---|
| HCT-M-02 | Central portion |
| HCT-C-08 | C-terminal portion |
| HCT-N-11 | N-terminal portion |
| HCT-C-15 | C-terminal portion |
| HCT-M-16 | Central portion |
| HCT-C-18 | C-terminal portion |

(3) Determination of antibody titer (affinity)

Firstly, 0.25 ng/ml of synthesized human calcitonin (50 µl) was added to each well of an ELISA plate (Costar) and allowed to react at 37° C. for one hour to immobilize the antigen to the wells. A blocking agent (300 µl) was then added to the wells and the wells were incubated at 37° C. for two hours. Then, the wells were thoroughly washed, and each of purified antibodies adjusted to 0.01 ng/ml to 1000 ng/ml of concentration (50 µl) was added to the wells and allowed to react at 37° C. for one hour. Then, a peroxidase-labelled anti-mouse IgG (recognizing H+L-chains) antibody (50 µl) was added to the wells and allowed to stand at room temperature for one hour. After thoroughly washing the wells, a 40% o-phenylenediamine solution (200 µl) containing 0.42% H$_2$O$_2$ was added to the wells and allowed to react at room temperature for 15 minutes. The reaction was then terminated by adding 3M sulfuric acid and absorbance was measured at 490 nm (measuring wavelength) and at 655 nm (control wavelength).

An antibody amount-reactivity curve was prepared (FIG. 1), and the reciprocal numbers of antibody concentrations (M) when OD490/OD655 is 1.0 under these conditions were taken as antibody titers. The monoclonal antibodies according to the present invention showed a high specificity to human calcitonin, as shown in Table 8.

TABLE 8

Antibody titer (affinity) of MAbs produced by six clones

| Clone name | Antibody titer (1/mole) |
|---|---|
| HCT-M-02 | $1.16 \times 10^{10}$ |
| HCT-C-08 | $6.47 \times 10^{10}$ |
| HCT-N-11 | $8.05 \times 10^{8}$ |
| HCT-C-15 | $1.80 \times 10^{10}$ |
| HCT-M-16 | $3.66 \times 10^{9}$ |
| HCT-C-18 | $1.29 \times 10^{11}$ |

As described above, monoclonal antibodies having a high affinity for human calcitonin were provided by the present invention. By utilizing the present monoclonal antibodies, it is possible to construct a sandwich immunoassay having a high sensitivity and a high accuracy for detecting human calcitonin.

What is claimed is:

1. A monoclonal antibody specifically recognizing human calcitonin which is produced by a hybridoma selected from the group consisting of hybridomas HCT-M-02 having accession number FERM BP-5750, HCT-C-08 having accession number FERM BP-5752, HCT-N-11 having accession number FERM BP 5749, HCT-C-15 having accession number FERM BP 5753, HCT-M-16 having accession number FERM BP 5751 and HCT-C-18 having accession number FERM BP 5754.

2. A hybridoma producing a monoclonal antibody specifically recognizing human calcitonin, which is selected from the group consisting of hybridomas HCT-M-02 having accession number FERM BP5750, HCT-C-08 having accession number FERM BP-5752, HCT-N-11 having accession number FERM BP-5749, HCT-C-15 having accession number FERM BP-5753, HCT-M-16 having accession number FERM BP-5751 and HCT-C-18 having accession number FERM BP-5751.

* * * * *